US006255356B1

(12) United States Patent
Butler

(10) Patent No.: US 6,255,356 B1
(45) Date of Patent: Jul. 3, 2001

(54) METHOD FOR INHIBITING FROM FEEDING, COCKROACHES

(75) Inventor: Jerry F. Butler, Gainesville, FL (US)

(73) Assignees: International Flavors & Fragrances Inc., New York, NY (US); The University of Florida, Gainesville, FL (US)

( * ) Notice: Subject to any disclaimer, the term of this patent is extended or adjusted under 35 U.S.C. 154(b) by 0 days.

(21) Appl. No.: 09/537,761

(22) Filed: Mar. 30, 2000

(51) Int. Cl.[7] .......................... A01N 31/00; A01N 31/02; A01N 27/00; A01N 65/00
(52) U.S. Cl. .......................... 514/739; 514/724; 514/763; 514/919; 424/DIG. 10
(58) Field of Search ..................................... 514/919, 546, 514/679, 739, 724, 763; 424/DIG. 10, 195.1

(56) References Cited

U.S. PATENT DOCUMENTS 4,774,081 * 9/1988 Flashinski et al. .................. 514/919
5,401,500 * 3/1995 Warren et al. ......................... 424/84
5,753,686   5/1998 Marin et al. .......................... 514/739

FOREIGN PATENT DOCUMENTS 2-67202 * 3/1990 (JP).
2-207004 * 8/1990 (JP).

* cited by examiner

Primary Examiner—John Pak
(74) Attorney, Agent, or Firm—Joseph F. Leightner

(57) ABSTRACT

Described is a method for inhibiting from feeding German cockroaches (*Blattella germanica*) from a surface or volume inhabited by said *Blattella germanica* consisting of the step of applying to said surface or said volume a *Blattella germanica*-anti-feedant quantity and concentration of a geraniol-containing mixture comprising:

(i) from about 0 up to about 20% by weight of nerol;
(ii) from about 20 up to about 40% by weight of citronellol; and
(iii) from about 50 up to about 70% by weight of geraniol, which geraniol-containing mixture is defined according to specific GLC profiles set forth in FIGS. 4 and 5, described in the disclosure. Also described are compositions of matter defined according to the geraniol-containing compositions of FIGS. 4 and 5 which act as anti-feedants against the German cockroach species set forth above.

4 Claims, 12 Drawing Sheets

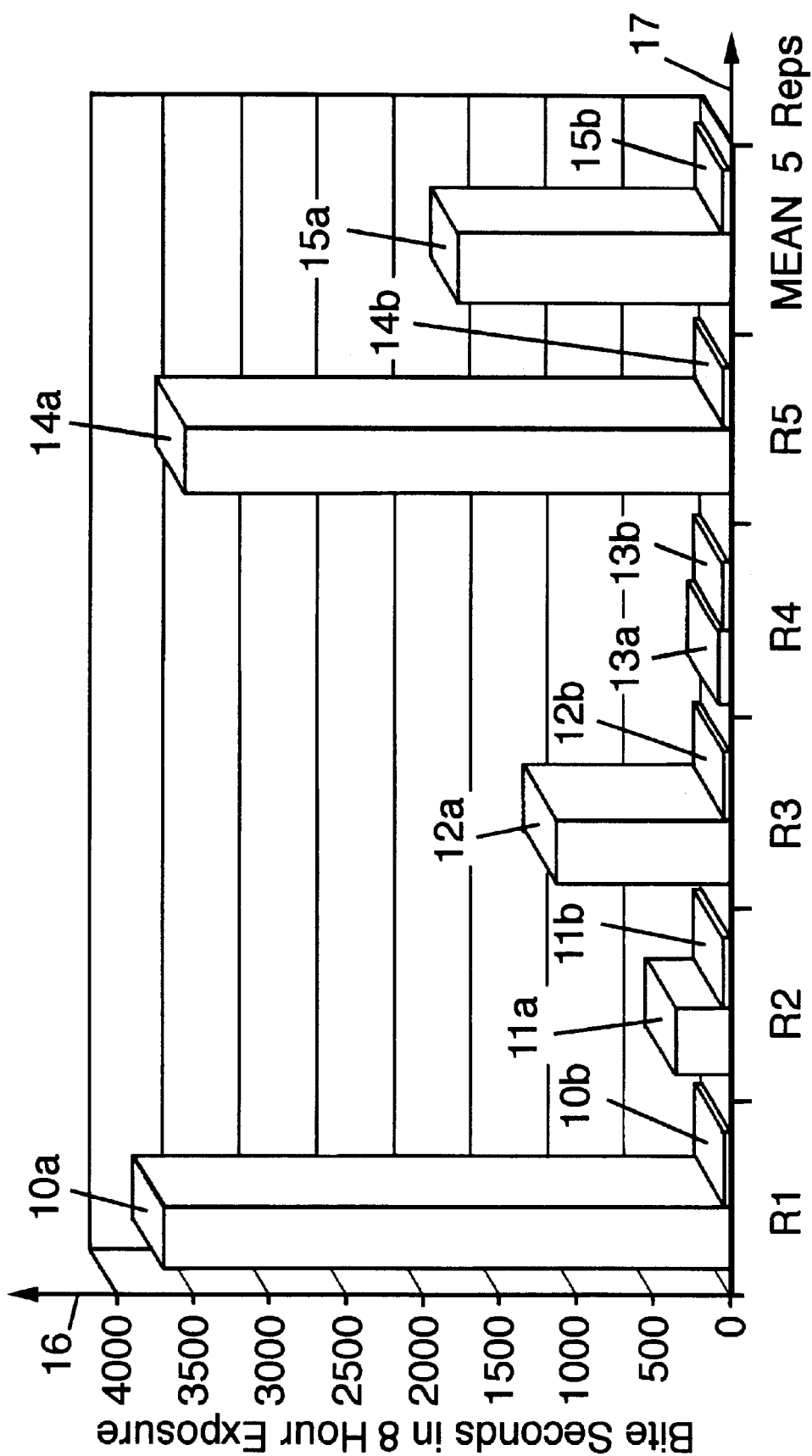

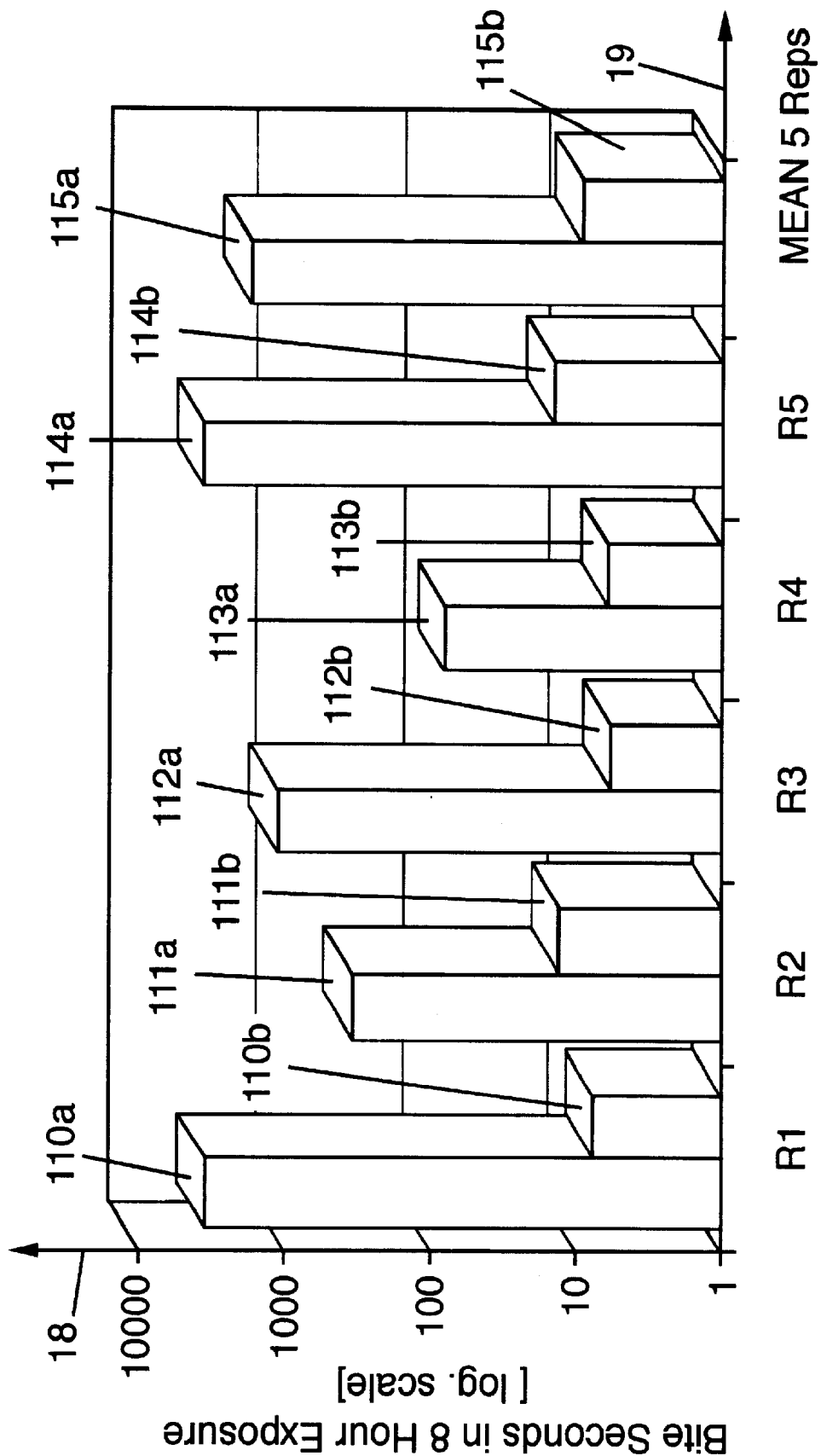
FIG.1-B

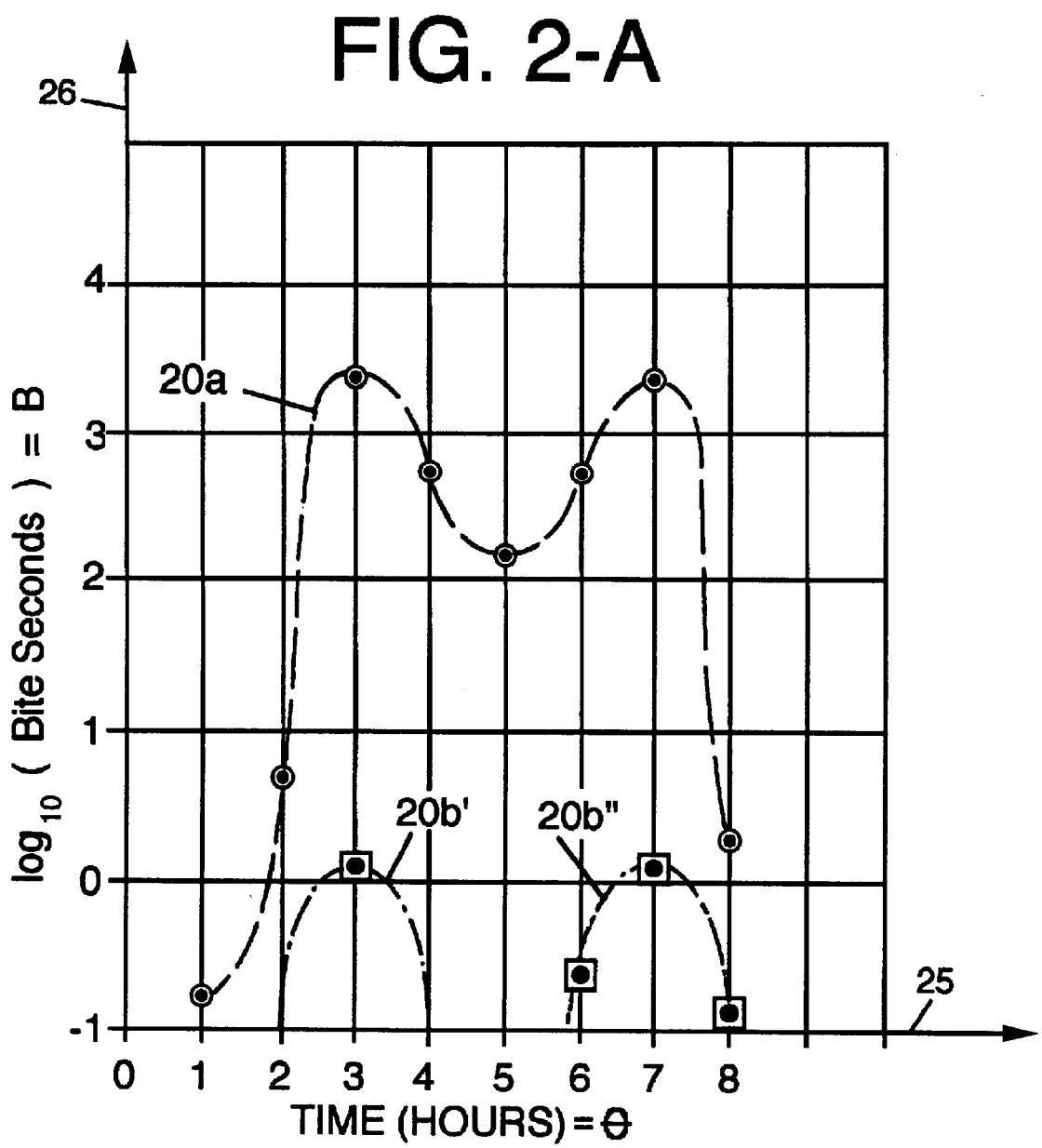

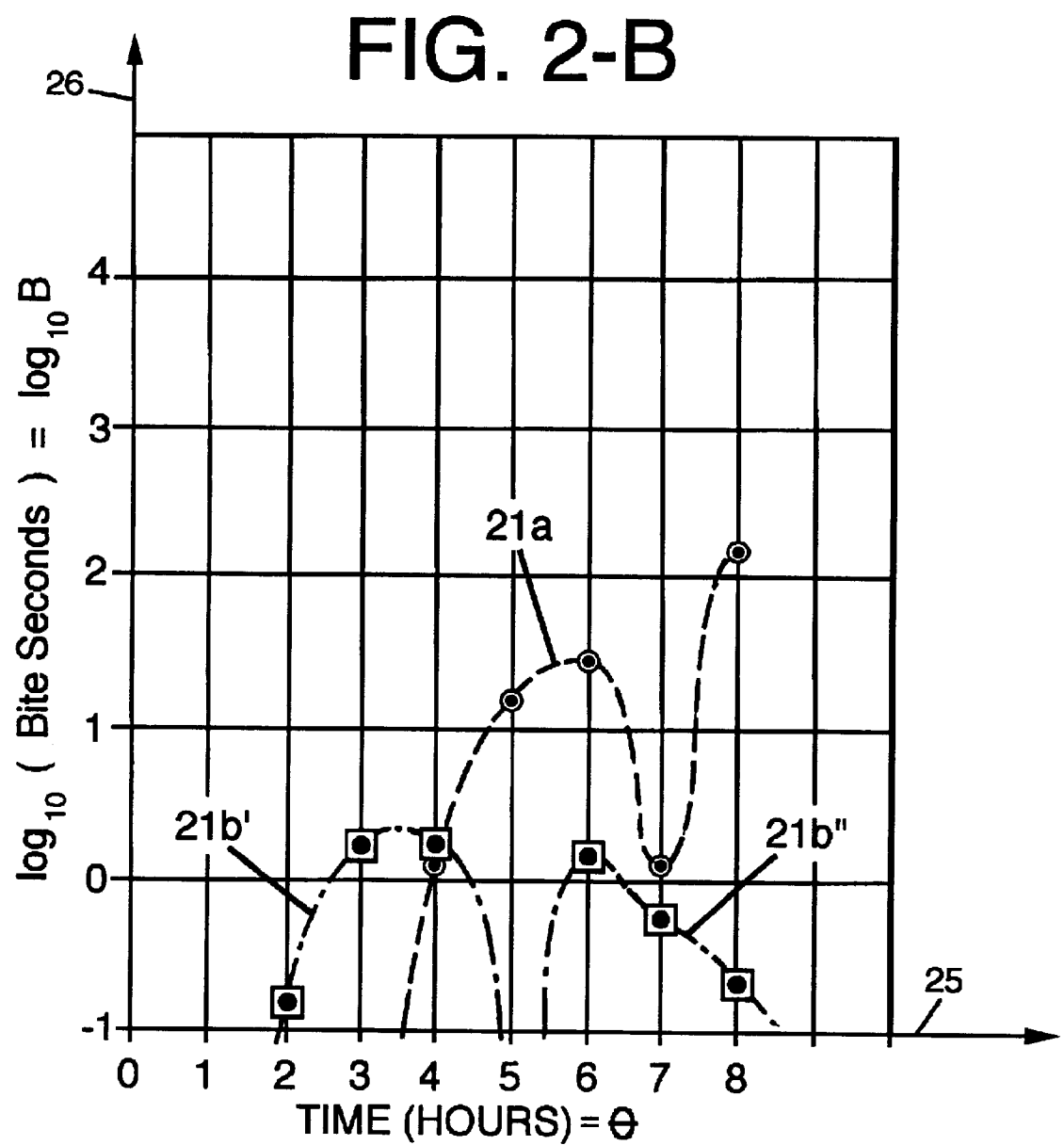

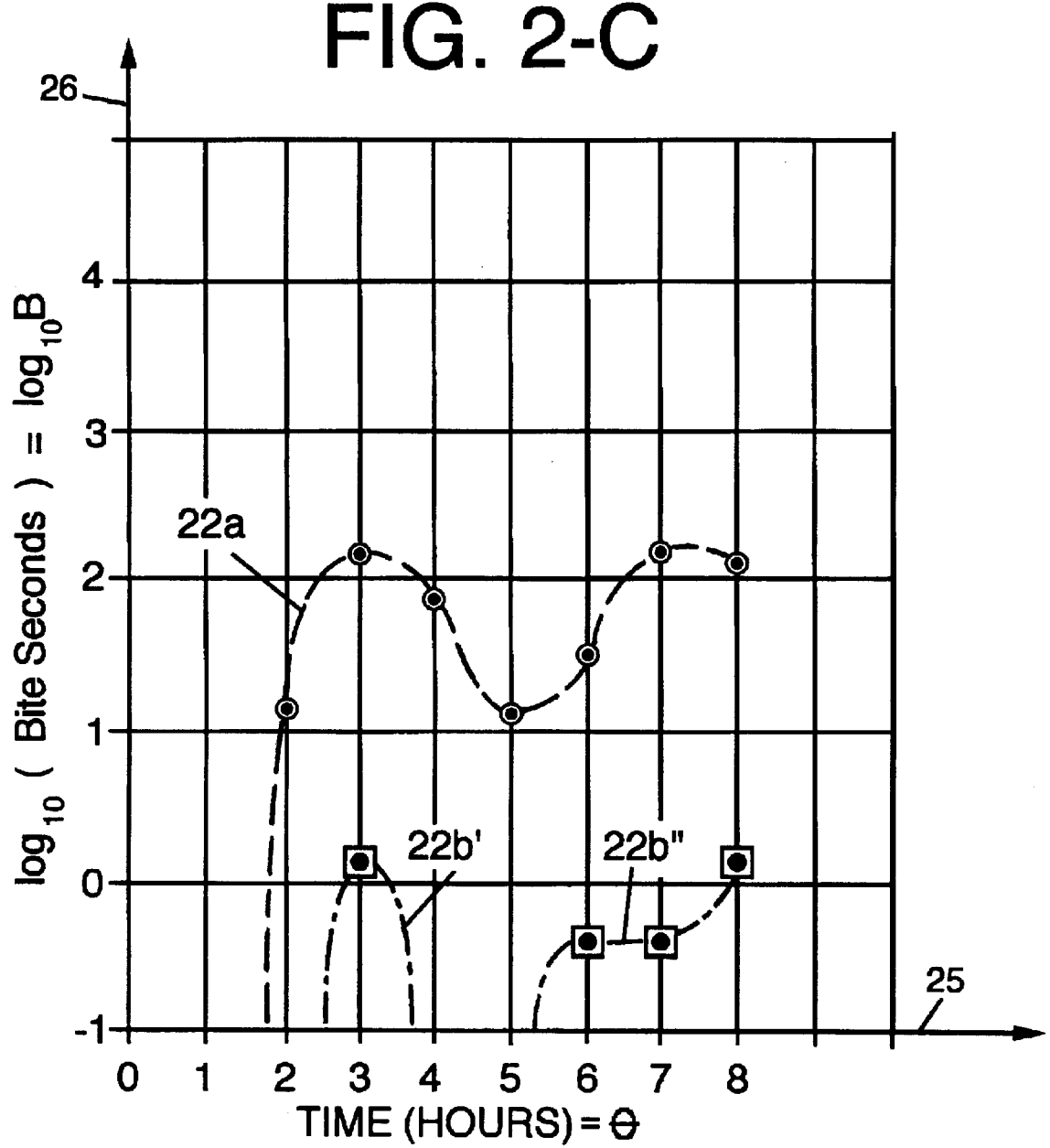

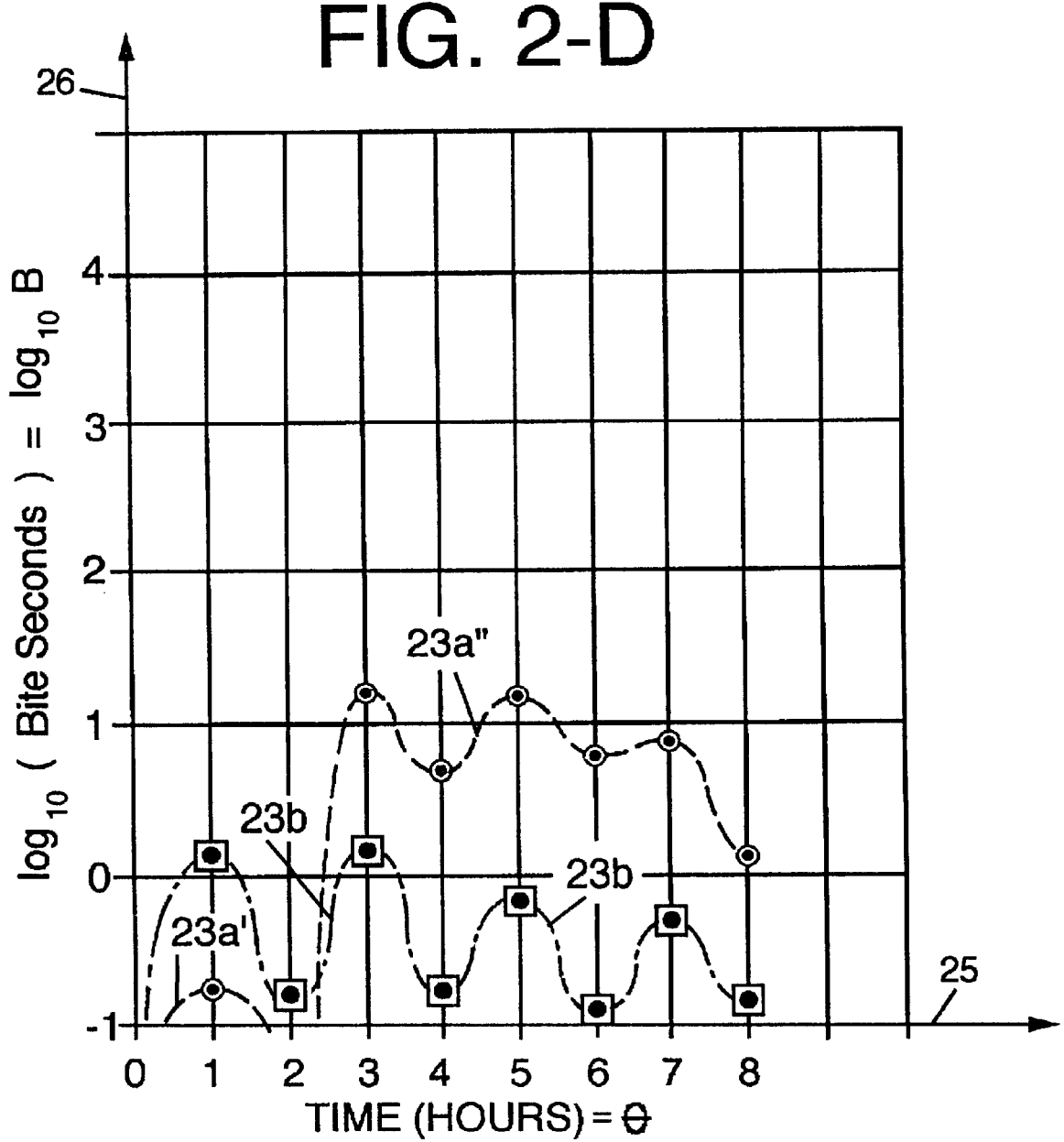
FIG. 2-D

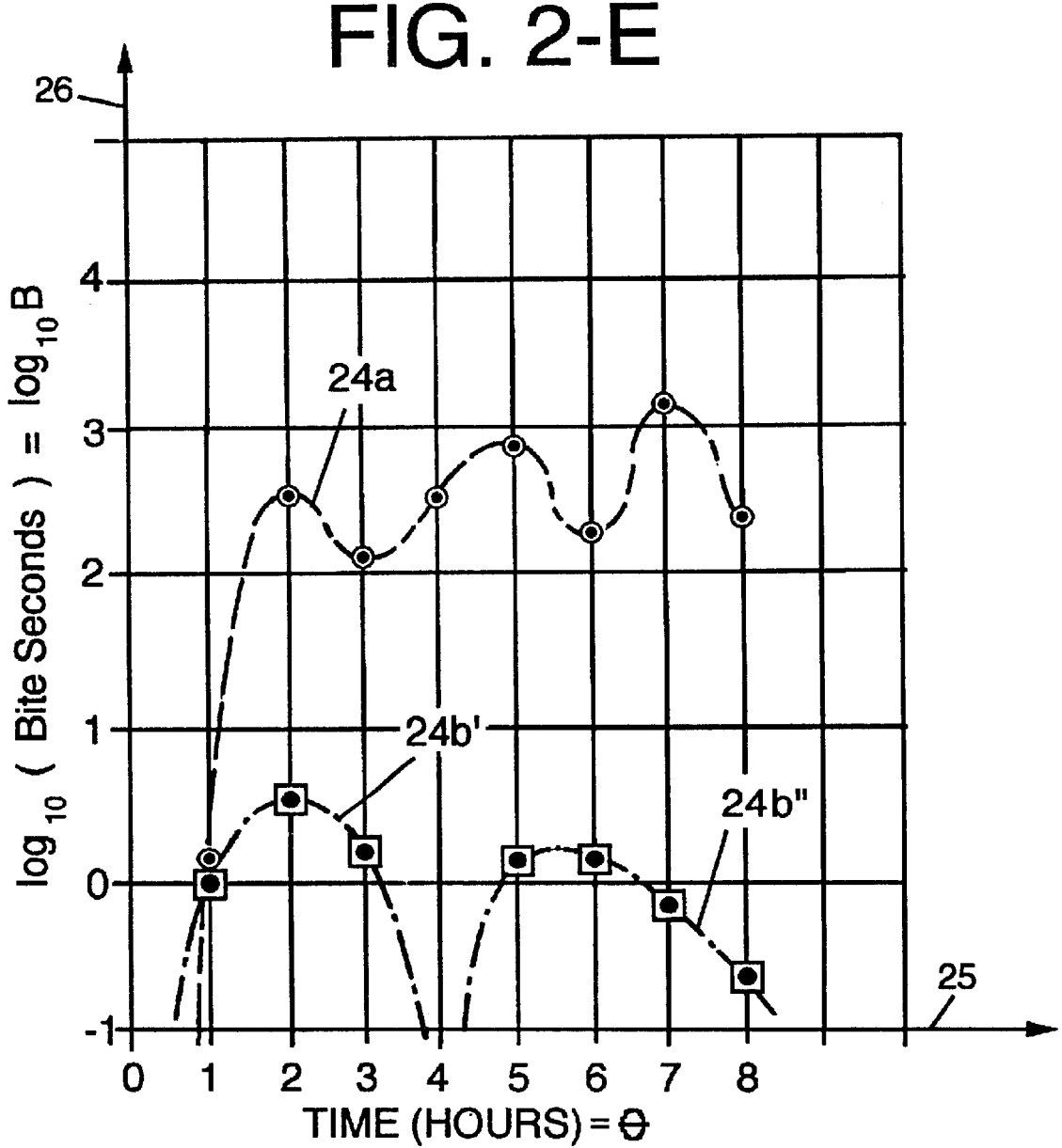
FIG. 2-E

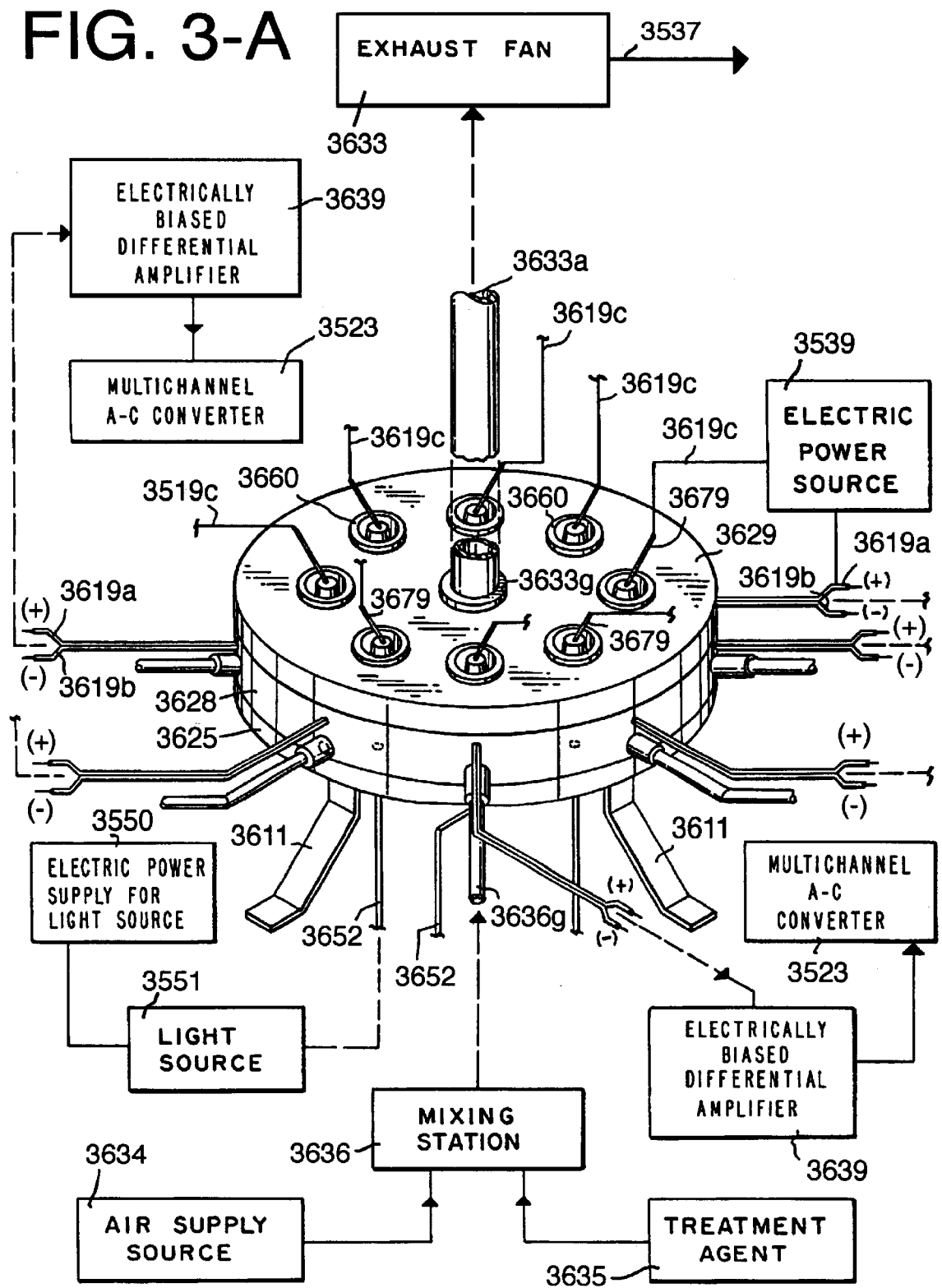

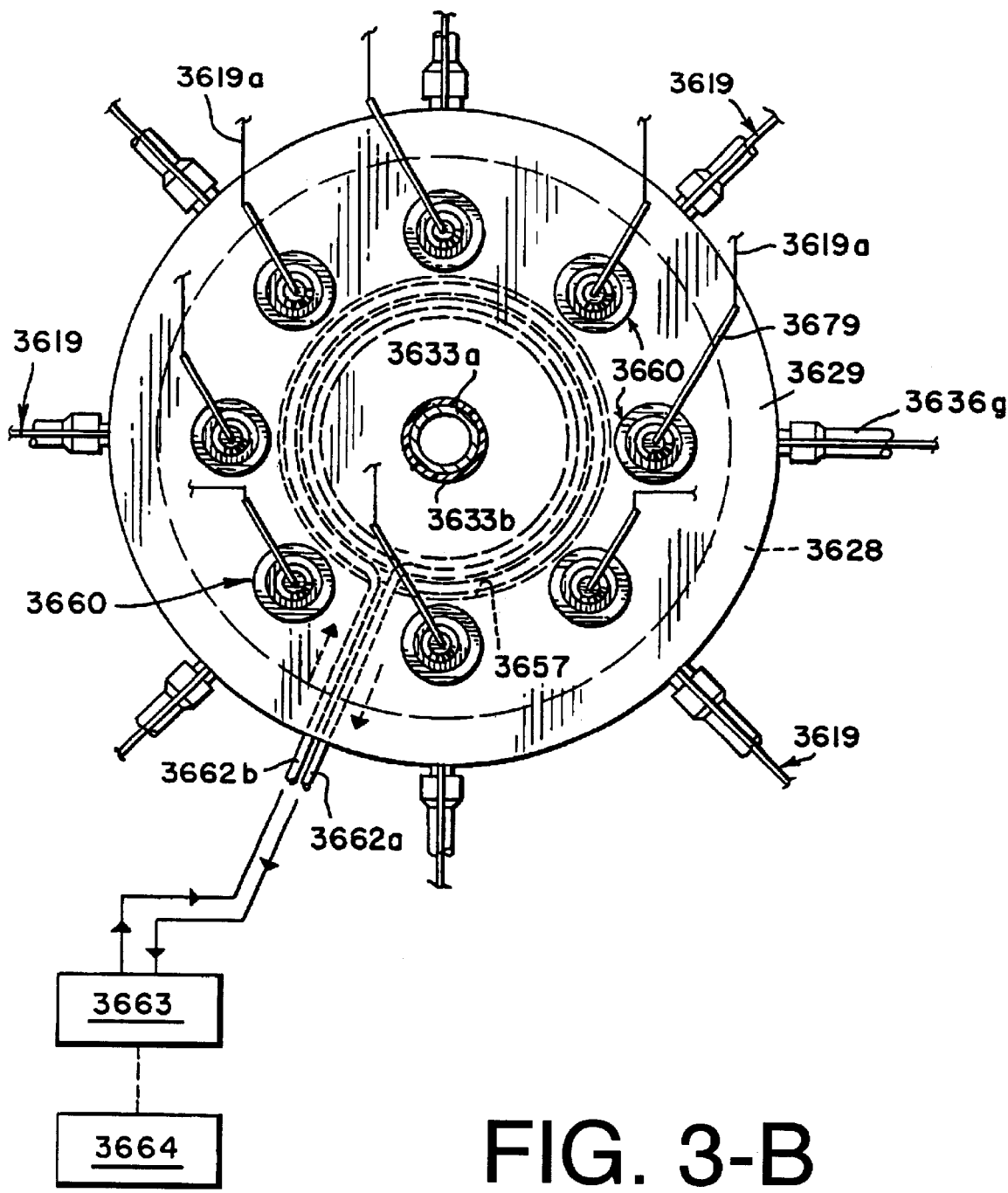
FIG. 3-B

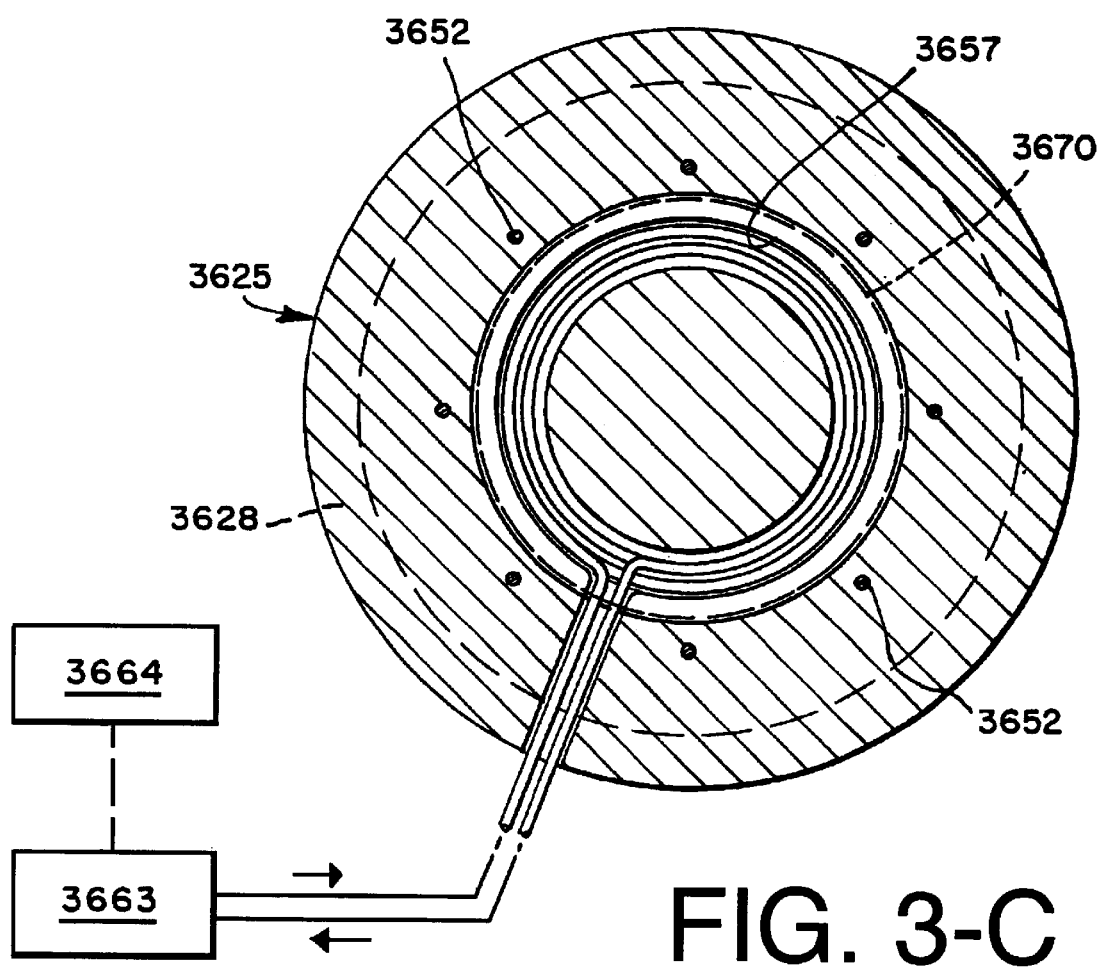
FIG. 3-C

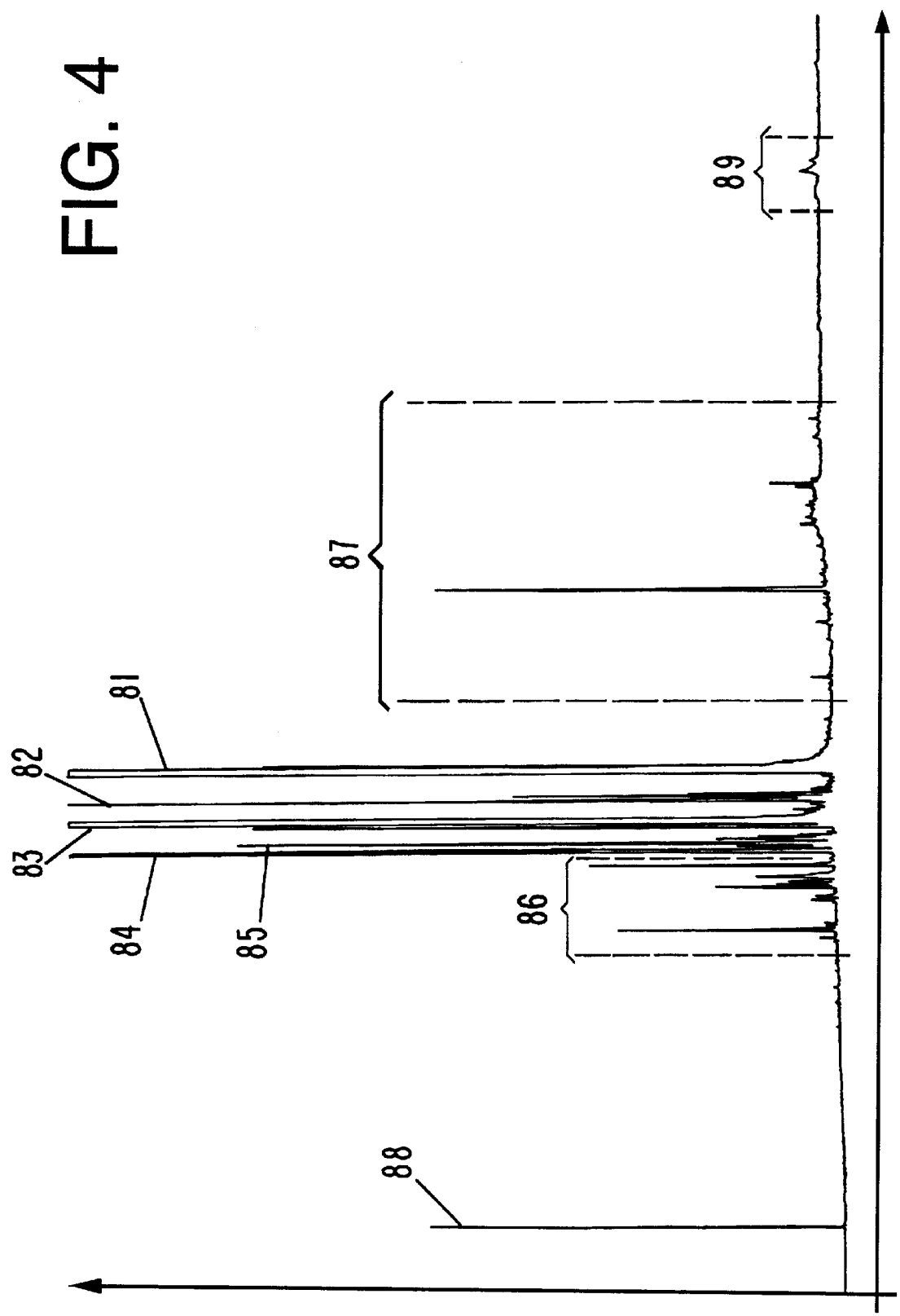

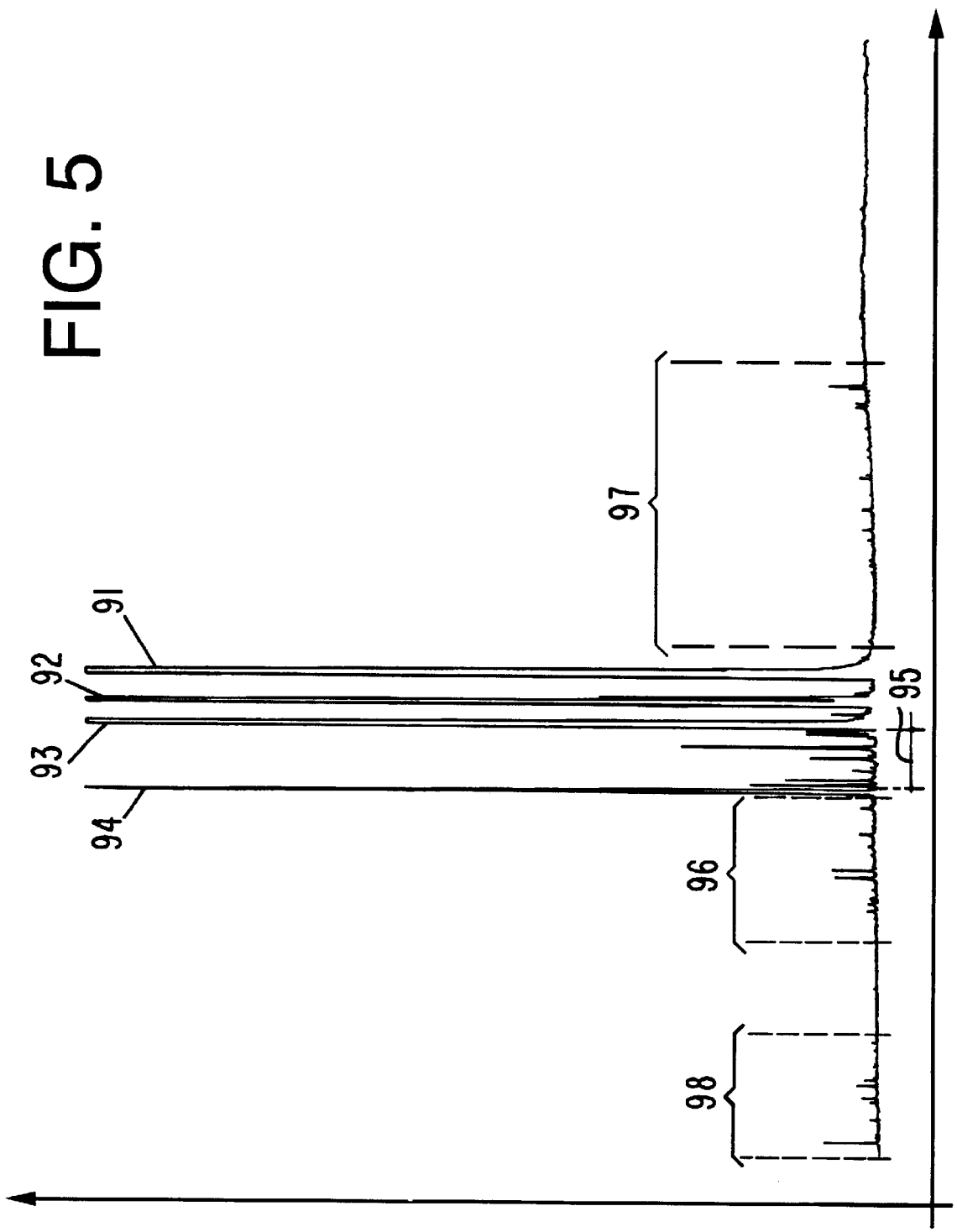

METHOD FOR INHIBITING FROM FEEDING, COCKROACHES

BACKGROUND OF THE INVENTION

My invention relates to methods of inhibiting from feeding the German cockroach (*Blattella germanica*) from a surface or volume inhabited by such insect species using as an anti-feedant composition materials known as "GERANIOL COEUR™" (trademark of International Flavors & Fragrances Inc.) defined according to the GLC profiles of FIGS. 4 and 5 and produced according to Examples, I and II, infra (also set forth herein as "geraniol-containing or geraniol-containing mixtures").

The "GERANIOL COEUR™" used in my invention comprises:

(i) from about 0 up to about 20% by weight of nerol;
(ii) from about 20 up to about 40% by weight of citronellol; and
(iii) from about 50 up to about 70% by weight of geraniol.

The GERANIOL COEUR™ used as an anti-feedant against such insect species can either be natural GERANIOL COEUR™ or synthetic GERANIOL COEUR™. Such GERANIOL COEUR™ compositions of matter contain a large number of additional chemicals, a number of which may be active in combination with the major components of the GERANIOL COEUR™, namely, the nerol, citronellol and geraniol and trace amounts of other materials.

The German cockroach (*Blattella germanica*) is known to cause health problems among various mammalian species and is a well known insect pest. Accordingly, a need exists for inhibiting from feeding such insect species, the German cockroach (*Blattella germanica*), from surfaces or volumes which are inhabited by such species and which are proximate the living space of mammalian species such as *Homo sapiens*.

GERANIOL COEUR™, both synthetic and natural, is described for use in repelling fire ants and horn flies in U.S. Pat. No. 5,753,686 issued on May 19, 1998, the specification for which is incorporated herein by reference. Described in said U.S. Pat. No. 5,753,686 is a method for repelling at least one of the insect species:

(i) *Haematobia irritans* (Linnaeus) (commonly known as the horn fly); and
(ii) *Solenopsis invicta* Buren (commonly known as the "red imported fire ant")

from a surface or volume inhabited by at least one of said insect species consisting of the step of applying to said surface or said volume a "red imported fire ant" and/or horn fly-repelling quantity and concentration of a geraniol-containing mixture comprising:

(i) from about 0 up to about 20% by weight of nerol;
(ii) from about 20 up to about 40% by weight of citronellol; and
(iii) from about 50 up to about 70% by weight of geraniol, which geraniol-containing mixture is defined according to specific GLC profiles, to wit, those set forth in FIGS. 4 and 5 of the instant specification.

Citronellol (both the "d" isomer and the "l" isomer) are described as weak repellents for the yellow-fever mosquito and *Aedes aegypti* in CHEMICALS EVALUATED AS INSECTICIDES AND REPELLENTS AT ORLANDO, FLA., King, U.S. Department of Agriculture, Agricultural Research, Agriculture Handbook No. 69, at page 120 (Items 3441 and 3442) (published May 1954).

"Geraniol" and various fractions of Java Citronella oil also described as "geraniol" are stated in the King reference at page 179 to be yellow-fever repellents and repellents for *Aëdes aegypti*. Reference is made to Items 5366 ("geraniol"); 5371 ("geraniol, first fraction of Java Citronella oil"); 5372 ("geraniol, second fraction of Java Citronella oil"); 5373 ("geraniol, last fraction of Java Citronella oil"); and 5374 ("geraniol, last fraction, high boiling, Java Citronella oil").

On the other hand, Beroza and Green, MATERIALS TESTED AS INSECT ATTRACTANTS, Agriculture Handbook No. 239, Agricultural Research Service, United States Department of Agriculture, June 1963, discloses 3,7-dimethyl octanol-1 having the strucuture:

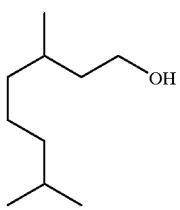

(Item 2883) as being an attractant for the oriental fruit fly, the melon fly and the Mediterranean fruit fly at a level of "1" on a scale of "1–3". The Beroza and Green reference also describes isomers of citronellol and geraniol as having attractancy for various insect species including the pink bollworm and the boll weevil. Thus, Items 2894, 2895 and 2875 for compounds having the structures:

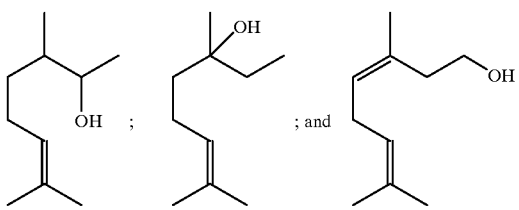

are shown by Beroza and Green to have weak attractancies for the oriental fruit fly, the melon fly, the Mediterranean fruit fly, the Mexican fruit fly, the gypsy moth, drosophila, the peak bollworm and the boll weevil at levels of "1" or "2" on a scale of "1–3".

Nothing in the prior art, however, teaches the inhibition from feeding against the German cockroach (*Blattella germanica*) of GERANIOL COEUR™ either natural or synthetic, and nothing in the prior art infers such anti-feedant properties.

THE INVENTION

My invention is directed to a method for inhibiting from feeding the German cockroach (*Blattella germanica*) from a surface or volume inhabited by the German cockroach (*Blattella germanica*) insect species consisting of the step of applying to said surface or said volume a German cockroach (*Blattella germanica*)-anti-feedant quantity and concentration of a geraniol-containing composition, GERANIOL COEUR™, natural (shown to be produced in Example I, infra) or synthetic (shown to be produced according to Example II, infra) comprising:

(i) from about 0 up to about 20% by weight of nerol;
(ii) from about 20 up to about 40% by weight of citronellol; and
(iii) from about 50 up to about 70% by weight of geraniol defined according to the GLC (gas liquid chromatography) profiles of FIGS. 4 and 5 described, infra. Such GERANIOL COEUR™ has a refractive index in the range of from about 1.45 up to about 1.48 and a density in the range of from about 0.85 up to about 0.88 at a temperature in the range of from about 20° C. up to about 25° C.

My invention is also directed to anti-feedant compositions containing such GERANIOL COEUR™, which compositions inhibit the feeding by said German cockroach (*Blattella germanica*). Accordingly, my invention is directed to a process for inhibiting feeding by the German cockroach (*Blattella germanica*) using the GERANIOL COEUR™ defined, supra.

The GERANIOL COEUR™ natural and GERANIOL COEUR™ synthetic compositions are similar but each has other chemical constituents in addition to the nerol, citronellol and geraniol and these constituents vary from the synthetic to the natural citronellol and geraniol and these constituents vary from the synthetic to the natural GERANIOL COEUR™. The additional constituents, for example, in the GERANIOL COEUR™, include but are not limited to 3,7-dimethyl octanol-1 having the structure:

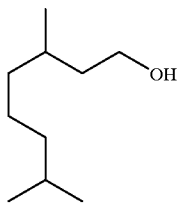

(found primarily in the synthetic GERANIOL COEUR™) and β-elemene having the structure:

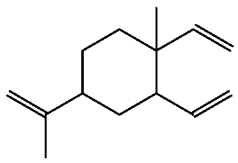

found in the natural GERANIOL COEUR™. The natural GERANIOL COEUR™'s GLC spectrum is set forth in FIG. 4 and synthetic GERANIOL COEUR™'s GLC spectrum is set forth in FIG. 5.

When discussing a "surface" inhabited by the *Blattella germanica*, such surface can be the skin of an animal such as a cow or the skin of a human being. When discussing the term "volume" inhabited by the *Blattella germanica*, such a volume would be an air space a human being, for example, or the volume could be a room into which a person will enter.

The coating of the GERANIOL COEUR™ onto the skin can be in several forms:

(i) in the form of an aerosol wherein the GERANIOL COEUR™ is incorporated into a standard aerosol formulation at the level of 0.05% up to about 5%; and (ii) in a non-toxic polymer such as polyvinyl alcohol or polyethylene or polypropylene at the levels of from about 1.0% of GERANIOL COEUR™ up to about 45% by weight of the polymer mixture of GERANIOL COEUR™.

Thus, my invention also contemplates anti-feedant formulations containing a base and incorporated into said base an anti-feedant quantity or concentration of GERANIOL COEUR™, the geraniol-containing mixture, defined according to the GLC spectra of FIGS. 4 or 5 as more specifically described, infra.

The term "citronellol" includes α-citronellol having the structure:

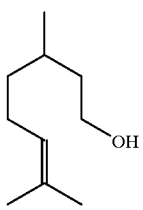

in both its "d" and "l" forms and β-citronellol having the structure:

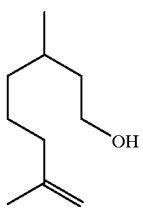

in both its "d" and "l" forms. GERANIOL COEUR™ natural and GERANIOL COEUR™ synthetic contain, primarily, the compound having the structure:

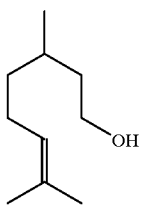

and, in lesser quantities, the compound having the structure:

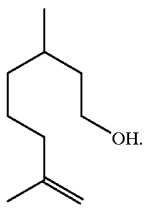

The GLC profiles in FIGS. 4 and 5 show both structures. The "d" and "l" forms of α-citronellol can be shown, thusly:

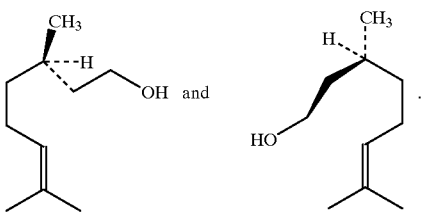

The term "geraniol" in this case is meant to indicate the compound having the structure:

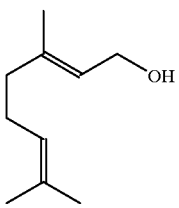

and no other compounds.

The term "nerol" in this application is intended to indicate the compound having the structure:

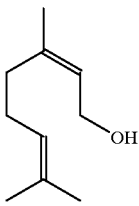

and no other compounds.

Thus, more specifically, my invention covers:

(i) a method for repelling German cockroaches (*Blattella germanica*) from a surface or volume inhabited by said German cockroaches (*Blattella germanica*) consisting of the step of applying to said surface or said volume a *Blattella germanica*-repelling quantity and concentration of GERANIOL COEUR™ defined according to one of the spectra of FIG. 4 or FIG. 5 or a mixture thereof; and (ii) an anti-feedant composition for inhibiting the feeding by said *Blattella germanica* from a feeding place which can be a skin surface or any other place where *Blattella germanica* feed, such as a food composition containing ingredients which attract, for the purpose of feeding, said *Blattella germanica*.

The GERANIOL COEUR™ so useful in my invention may be applied in the form of an insect repellent cream, or in the form of an aerosol spray (as indicated, supra) or may be placed into a candle body and may be applied to a volume by means of the use of a burning candle as set forth, for example, at columns 35 and 36 of U.S. Pat. No. 5,175,175 issued on Dec. 29, 1992, the specification for which is incorporated herein by reference. Furthermore, the GERANIOL COEUR™ so useful in my invention may be slowly and controllably released into a volume inhabited by *Blattella germanica* by means of first incorporating the GERANIOL COEUR™ (natural or synthetic or mixtures thereof) into a control release polymer such as microporous polyethylene or microporous polypropylene or microporous polyurythane in accordance with the process set forth at columns 30, 31, 32, 33 and 34 of U.S. Pat. No. 5,175,175 issued on Dec. 29, 1992, the specification for which is incorporated by reference herein.

The GERANIOL COEUR™ so useful in my invention may also be incorporated into a soap base wherein soap articles can be prepared according to the specification of Application for U.S. patent Ser. No. 824,591 filed on Jan. 23, 1992, the specification for which is incorporated by reference herein.

The GERANIOL COEUR™ so useful in my invention may also be combined with other insect-repelling or non-attracting perfume bases whereby the overall composition will repel the *Blattella germanica*. Such insect-repelling bases can be prepared according to the teachings of Application for U.S. patent Ser. No. 691,635 filed on Apr. 25, 1991 (now abandoned), the specification for which is incorporated by reference herein as well as in accordance with U.S. Pat. No. 5,228,233 issued on Jul. 20, 1993, the specification for which is incorporated by reference herein.

BRIEF DESCRIPTION OF THE DRAWINGS

FIGS. 1A and 1B are three-dimensional bar graphs showing testing of well known attractants and mixtures of well known attractants with GERANIOL COEUR™ using the laboratory olfactometer as set forth in schematic form in FIGS. 3A, 3B and 3C. FIG. 1A shows a series of bar graphs along the X axis for five replications of comparative experiments as set forth in Tables I and II described, infra. FIG. 1B shows the same data whereby the bite seconds in 8 hour exposure on the Y axis is shown using a log (base 10) scale. The data for these graphs is set forth in Table II described in detail, infa, in the "Detailed Description of the Drawings" section of the instant specification, infra.

FIGS. 2A, 2B, 2C, 2D and 2E set forth graphs in two dimensions showing on the Y axis $\log_{10}$ (bite seconds) for the *Blattella germanica* being attracted to either (a) a standard attractant composed of agar and blood and (b) the same standard attractant with a coating of GERANIOL COEUR™ thereon, with the X axis being time in hours. Each of FIGS. 2A, 2B, 2C, 2D and 2E sets forth a replication of the comparative experiments over a period of 8 hours. Each of the replications is set forth in detail in Table I, contained within the section of the instant specification entitled "Detailed Description of the Drawings," infra.

FIG. 3A is a schematic diagram (blown up for illustration purposes) of olfactometer apparatus useful in ascertainig the efficacy of, inter alia, GERANIOL COEUR™ as a repellent for German cockroaches (*Blattella germanica*) indicating in schematic block flow diagram form the utilization of computer assisted efficacy measuring apparatus; and also showing in block flow diagram form the interrelationship of air and treatment agent mixing station with entry ports for the resulting air-treatment mixture into the olfactometer apparatus. This olfactometer apparatus is described in detail in U.S. Pat. No. 5,175,175 issued on Dec. 29, 1992, the specification for which is incorporated by reference herein.

FIG. 3B is a top view of a base section of an embodiment of the olfactometer apparatus set forth in FIG. 3A showing means for raising the temperature of the insect feeding and/or stimulating means using heating coils.

FIG. 3C is a cut-away cross sectional bottom view of the embodiment of the olfactometer apparatus used in my invention shown, in part, in FIG. 3B showing in detail the location of the heating coil means in the base section of the olfactometer apparatus used for testing.

FIG. 4 is the GLC profile of GERANIOL COEUR™ natural produced according to Example I, infra (conditions: dual fused silica system programmed from 70–270° C. at 4° C. per minute).

FIG. 5 is the GLC profile for GERANIOL COEUR™ synthetic produced according to Example II, infra (conditions: dual fused silica system programmed from 70–220° C. at 4° C. per minute).

DETAILED DESCRIPTION OF THE DRAWINGS

In the following Tables I and II, comparisons are carried out between the attractancy or repellency of the German cockroach (Blattella germanica) to:

(a) a standard attractant, 1 cm in diameter×0.4 cm in thickness, which is composed of a blood/agar base as described in the doctoral thesis by Douglas A. Burkett entitled "Light Color Attraction and Dietary Sugar Composition for Several Mosquito (Diptera culicidae) species in North Central Florida," University of Florida, 1998; and (b) the same standard attractant disk, 1 cm in diameter× 0.4 cm in thickness coated with a silicone membrane, which is porous on which is coated 0.002 grams of either GERANIOL COEUR™ (synthetic) or GERANIOL COEUR™ (natural) as produced according to Example I or Example II or 50-50 mixtures of same.

Whether GERANIOL COEUR™ (natural) or GERANIOL COEUR™ (synthetic) is used or whether 50-50 mixtures are used, the overall results are substantially identical.

Table I, set forth below, shows in detail data also depicted graphically in FIGS. 2A, 2B, 2C, 2D and 2E for five replications, each replication showing a comparison between the standard attractant as described, supra, and the same standard attractant being coated thereon with a silicone membrane which, in turn, is coated with the GERANIOL COEUR™, either synthetic, natural or a mixture of 50% synthetic and 50% natural GERANIOL COEUR™.

From a statistical analysis standpoint, the data has a 0.025 T-Test significance level.

Table II sets forth the sum or mean of the 8 hour, bite second feeding response data shown in detail in Table I. The results of Table II are set forth on a standard three-dimensional bar graph in FIG. 1A and are set forth in a semi-logarithmic bar graph form in FIG. 1B, with the sum or mean of the 8 hour, bite second response on the V axis being on a log (base 10) scale.

The data set forth in Tables I and II is for tests using the laboratory olfactometer described in detail, infra, and set forth in FIGS. 3A, 3B and 3C.

Table I is as follows, referring to FIGS. 2A, 2B, 2C, 2D and 2E described in detail infra:

TABLE I

| Time Interval (Hours) | First Replication as Shown in FIG. 2A | | Second Replication as Shown in FIG. 2B | | Third Replication as Shown in FIG. 2C | | Fourth Replication as Shown in FIG. 2D | | Fifth Replication as Shown in FIG. 2E | |
|---|---|---|---|---|---|---|---|---|---|---|
| | Attractant Only | GERANIOL COEUR™ Coated on Silicone Coated on Attractant | Attractant Only | GERANIOL COEUR™ Coated on Silicone Coated on Attractant | Attractant Only | GERANIOL COEUR™ Coated on Silicone Coated on Attractant | Attractant Only | GERANIOL COEUR™ Coated on Silicone Coated on Attractant | Attractant Only | GERANIOL COEUR™ Coated on Silicone Coated on Attractant |
| 0:00 | 0 | 0 | 0 | 0 | 0 | 0 | 0 | 0 | 0 | 0 |
| 1:00 | 0.3 | 0 | 0 | 0.11 | 0 | 0 | 0.4 | 1.21 | 3.01 | 1.39 |
| 2:00 | 56.13 | 0 | 0 | 0 | 16.67 | 0 | 0 | 0.2 | 422.85 | 6.11 |
| 3:00 | 1305.65 | 3.06 | 0 | 3.6 | 444.24 | 2.42 | 17.39 | 2.28 | 171.67 | 2.17 |
| 4:00 | 567.48 | 0 | 1.3 | 4.48 | 76.06 | 0 | 5.86 | 0.39 | 355.38 | 0 |
| 5;00 | 113.42 | 0 | 32.2 | 0 | 13.88 | 0 | 34.17 | 0.8 | 961.34 | 1.41 |
| 6:00 | 329.4 | 0.39 | 68.63 | 3.52 | 49.43 | 0.79 | 7.05 | 0.09 | 202.34 | 1.3 |
| 7:00 | 1301.11 | 3.9 | 7.38 | 0.89 | 414.15 | 0.7 | 9.85 | 0.6 | 1096.14 | 0.98 |
| 8:00 | 29.51 | 0.19 | 234.49 | 0.2 | 119.11 | 1.64 | 3.7 | 0.31 | 325.95 | 0.6 |

TABLE II

SUM OR MEAN OF THE 8 HOUR, BITE SECOND FEEDING RESPONSE

| | Replication No. 1 | Replication No. 2 | Replication No. 3 | Replication No. 4 | Replication No. 5 | Mean of the 5 Replications |
|---|---|---|---|---|---|---|
| The Sum or Mean without Repellent | 3703 | 344 | 1133.54 | 78.42 | 3538.68 | 1759.53 |

TABLE II-continued

SUM OR MEAN OF THE 8 HOUR, BITE SECOND FEEDING RESPONSE

|  | Replication No. 1 | Replication No. 2 | Replication No. 3 | Replication No. 4 | Replication No. 5 | Mean of the 5 Replications |
|---|---|---|---|---|---|---|
| The Sum or Mean with Repellent Coated on Attractant | 7.54 | 12.8 | 5.55 | 5.88 | 13.96 | 9.146 |
| Sum of Actives | 3710.54 | 356.8 | 1139.09 | 84.34 | 3552.64 | 1768.67 |

Referring now to FIG. 1A, the bar graphs indicated by reference numerals 10a and 10b are the bar graphs for the first replication, with bar graph 10a being the data generated for bite seconds in the 8 hour exposure for the standard attractant only and the bar graph indicated by reference numeral 10b being for the bite seconds in the 8 hour exposure for the standard attractant coated with a silicone membrane on which is coated the GERANIOL COEUR™.

The bar graphs indicated by 11a and 11b are for the second replication as shown in Table II.

The bar graphs indicated by reference numerals 12a and 12b are for the third replication as shown in Table II, supra.

The bar graphs indicated by reference numerals 13a and 13b are for the fourth replication as shown in Table II, supra.

The bar graphs indicated by reference numerals 14a and 14b are for the fifth replication as shown in Table II, supra.

The bar graphs indicated by reference numerals 15a and 15b are for the mean of the five replications also as shown in Table II, supra.

The same data where the bite seconds for the 8 hour exposure is on a log (base 10) scale on the Y axis is set forth in FIG. 1B.

Thus, the first replication data using standard attractant only is shown by the bar graph indicated by reference numeral 110a in FIG. 1B, and the bar graph showing the data generated wherein the standard attractant is coated with a silicone membrane which in turn is coated with GERANIOL COEUR™ for the first replication is shown by reference numeral 110b.

The data for the second replication in FIG. 1B is shown using the bar graphs indicated by reference numerals 111a and 111b.

The data for FIG. 1B for the third replication is shown using the bar graphs indicated by reference numerals 112a and 112b.

The data for FIG. 1B for the fourth replication is shown using the bar graphs indicated by reference numerals 113a and 113b.

The data for the fifth replication for FIG. 1B is shown using the bar graphs indicated by reference numerals 114a and 114b.

The data for the mean of the five replications for FIG. 1B is shown using the bar graphs indicated by reference numerals 115a and 115b, with the bar graph indicated by reference numeral 115a being for the use of the standard attractant only and the bar graph indicated by reference numeral 115b being for the use of the standard attractant coated with a silicone membrane which in turn is coated with the GERANIOL COEUR™.

With respect to FIG. 1A, the Y axis is indicated by reference numeral 16 and is for the sum or mean of the 8 hour bite second feeding response for each of the five replications nd the mean of the five replications. The X axis shows the five replications and the mean of the five replications thereon.

In FIG. 1B, the Y axis is for the sum or mean of the 8 hour bite second feeding response for the German cockroach (*Blattella germanica*) on a log (base 10) scale, and the Y axis is indicated by reference numeral 18. The X axis in FIG. 1B shows the five replications and the mean of the five replications and is indicated by reference numeral 19.

The detailed data as stated, supra, for Table I is set forth in FIGS. 2A, 2B, 2C, 2D and 2E. These Figures are referred to in Table I.

Thus, in FIGS. 2A, 2B, 2C, 2D and 2E, the Y axis which is:

$$\log_{10}[\text{BITE SECONDS}]=\log_{10}B,$$

and the X axis is time in hours represented by the symbol: θ.

In FIG. 2A, the graph indicated by reference numeral 20a is for the data wherein only standard attractant (blood/agar mixture) is used. The graphs indicated by reference numerals 20b' and 20b" are for the data wherein the standard attractant is coated with a silicone membrane which in turn is coated with GERANIOL COEUR™.

By the same token, the graph in FIG. 2B indicated by reference numeral 21a is for the data generated for German cockroaches (*Blattella germanica*) using standard attractant only, and the data indicated by the graphs indicated by reference numerals 21b' and 21b" is for the attractancy for German cockroaches (*Blattella germanica*) using standard attractant coated with a silicone membrane coated with GERANIOL COEUR™.

By the same token, in FIG. 2C, the graph indicated by reference numeral 22a is for the data for the attractancy of German cockroaches (*Blattella germanica*) to the mixture which is only attractant (blood/agar mixture), whereas the graphs indicated by reference numerals 22b' and 22b" are for the attractancy data for the German cockroaches (*Blattella germanica*) to the agar/blood mixture coated with a silicone membrane coated with the GERANIOL COEUR™.

By the same token, the graphs indicated by reference numerals 23a' and 23a" in FIG. 2D are for the attractancy of German cockroaches (*Blattella germanica*) to the standard attractant mixture (without GERANIOL COEUR™ repellent coated thereon). The graph indicated by reference numeral 23b in FIG. 2D is for the data for the attractancy of the German cockroaches (*Blattella germanica*) to the standard attractant mixture coated with a silicone membrane on which is coated the GERANIOL COEUR™.

The graph indicated by reference numeral 24a in FIG. 2E is for the data for the attractancy of the German cockroaches (*Blattella germanica*) to the standard attractant (blood/agar) mixture (without GERANIOL COEUR™ coated thereon). The graphs indicated by reference numerals 24b' and 24b" are for the data for the attractancy of the German cockroaches (*Blattella germanica*) to the blood/agar (standard attractant) mixture having coated thereon a silicone membrane having coated thereon in turn the GERANIOL COEUR™.

The equations for the attractancy to the standard attractant of the German cockroach (*Blattella germanica*) can be shown in general according to the equation:

$$\log_{10} B = \alpha\theta^n + \beta\theta^{n-1} + \gamma\theta^{n-2} + \delta\theta^{n-3} + \epsilon\theta^{n-4} + \ldots + \omega\theta^{n-k}$$

wherein B are the bite seconds as defined, supra; n is an integer of from 1 up to 6; and k is an integer of from 1 up to 6; with $\alpha, \beta, \gamma, \delta, \epsilon$ and $\omega$ being constants; with the proviso that k is less than or equal to ($\leq$) n, but greater than or equal to ($\geq$) 0 according to the inequality:

$$n \geq k \geq 0.$$

The equation:

$$\log_{10} B = \alpha\theta^4 + \beta\theta^3 + \gamma\theta^2 + \delta\theta + \epsilon$$

is an example of a more specific equation fitting, for example, the data of FIG. 2A for the attractancy of the German cockroach (*Blattella germanica*) to the standard attractant (without having coated thereon the GERANIOL COEUR™). An example of an equation for the attractancy of the German cockroach (*Blattella germanica*) to the standard attractant coated with silicone membrane which in turn is coated with GERANIOL COEUR™ is as follows:

$$\log_{10} B = \alpha\pi \, sin^p\theta + \beta\pi \, sin^{p-1}\theta + \gamma\theta^p + \delta\theta^{p-1} + \epsilon$$

wherein p is 2 or 3.

The laboratory olfactometer apparatus of FIGS. 3A, 3B and 3C is operated without engaging electric power supply for light source 3550 (for light source 3551). Thus, the tests are all carried out in the absence of light.

FIG. 3A sets forth in perspective an exploded view of the olfactometer apparatus used in testing the efficacy of, for example, GERANIOL COEUR™ natural or the GERANIOL COEUR™ synthetic against the German cockroach (*Blattella germanica*).

Air supply source 3634 provides air to mixing station 3636 wherein the air is mixed with treatment agent from treatment agent source 3635 (source of, for example, GERANIOL COEUR™ natural). The resulting mixture passes through tube 3636g (for example) and enters the apparatus through side portals. The entry is through spacer plate 3628 and above base plate 3625. The entry of the air-treatment agent is in a direction parallel to the surface of the base plate 3625. Thus, the base plate 3625 is separated from the spacer plate 3629 by entry section 3628 having portals for the air-treatment agent (for example, GERANIOL COEUR™ natural or GERANIOL COEUR™ synthetic) entering through lines 3636g. Air exits through line 3633a using exhaust fan 3633. The air exit is indicated by reference numeral 3537.

In several tests, but not in the instant one, simultaneously with the supplying of air and treatment agent from mixing station 3636, light could be supplied from beneath the enclosed insect feeding and/or stimulating means collectively denoted as "IFS" means through light guides 3652 from light source 3551 which could be powered by electric power supply 3550. Air supply from location 3634 and treatment agent from location 3635 is mixed at mixing station 3636 whereupon treatment agent and air in admixture is passed through lines 3636g through portals located in the spacer element 3628 in a direction along a directional vector parallel to the electrical sensing element located directly below the horizontally positioned insect feeding and/or stimulating microporous substantially planar lamina held in place by ring 3660 located on spacer plate 3629 spaced from the base plate 3625 by spacer ring 3628. It should be noted that the spacer plate 3629, spacer rings 3628 and base plate 3625 enclose the entire enclosed insect feeding and/or stimulating means collectively denoted as "IFS" means which have controlled limited access to the external environment surrounding the apparatus and in which the insects to be tested, e.g., German cockroaches (*Blattella germanica*) are placed. The apparatus so useful in carrying out the tests for my invention is fully described in U.S. Pat. No. 5,175,175 issued on Dec. 29, 1992, the specification for which is incorporated herein by reference.

FIGS. 3B and 3C show the use of heating elements located in base plate 3625. Thus, in FIG. 3B heating coils 3662a and 3662b are located in base plate 3625. Air and treatment agent are fed into portals located in spacing ring 3628 (but for the purposes of the instant case, no radiation is transmitted through light guides 3652 which are held in place on base plate 3625). Base plate 3625 is spaced at a reasonable distance (e.g., 1.0 inches) using spacer ring 3628 which is sealed in place using silicone seals, for example. In FIG. 3C, a well for the heating coils 3662a and 3662b is contained in base plate 3625 and is indicated by reference numeral 3657. Base plate 3625 is located on a stand which is situated on dampers 3611. The top view of the olfactometer looking down on the face plate 3629 is set forth in FIG. 3B. The reference numeral 3629 refers to the face plate per se. Hidden lines 3662a and 3662b are representations of the heating coils through which heat transfer fluid is supplied through lines 3662a and 3662b (with heated water) using pump 3663, the heat for which is controlled using controller 3664. Coils 3662a and 3662b are preferably covered at cavity 3657 with a heat transfer paste. FIG. 3C is also a top view of the olfactometer with the face plate removed looking directly down on the base plate 3625.

From the foregoing Tables I and II, which correspond to the graphs of FIGS. 1A, 1B, 2A, 2B, 2C, 2D and 2E, it is evident that the GERANIOL COEUR™ synthetic and the GERANIOL COEUR™ natural according to the GLC profiles of FIGS. 4 and 5 are excellent repellents against German cockroaches (*Blattella germanica*).

FIG. 4 is the GLC profile for GERANIOL COEUR™ natural produced according to Example I, infra. The peak indicated by reference numeral 81 is the peak for geraniol having the structure:

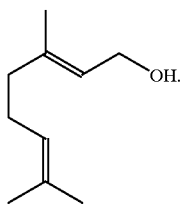

The peak indicated by reference numeral 82 is for nerol having the structure:

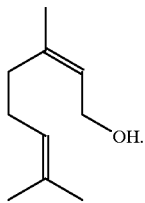

The peak indicated by reference numeral 83 is for α-citronellol having the structure:

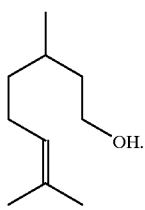

The peaks indicated by reference numerals 84 and 85 are for β-citronellol having the structure:

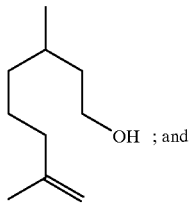

in addition, 3,7-dimethyl octanol-1 having the structure:

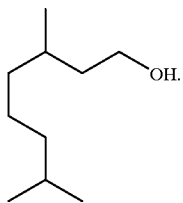

Other materials also are contained in GERANIOL COEUR™ but are of unknown chemical constituency and those are the peaks indicated by reference numerals 86, 87, 88 and 89. Included in the peaks indicated by reference numeral 87 is the compound β-elemene having the structure:

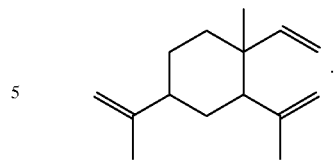

FIG. 5 is the GLC profile for GERANIOL COEUR™ synthetic (produced according to Example II, infra). The peak indicated by reference numeral 91 is the peak for geraniol having the structure:

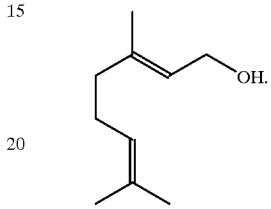

The peak indicated by reference numeral 92 is the peak for nerol having the structure:

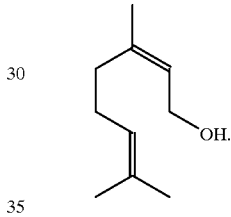

The peak indicated by reference numeral 93 is the peak for α-citronellol having the structure:

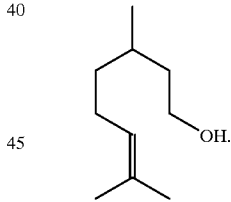

The peak indicated by reference numeral 94 is the peak for 3,7-dimethyl octanol-1 having the structure:

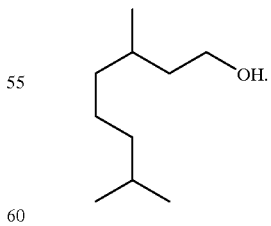

The peaks indicated by reference numerals 95, 96, 97 and 98 are for additional materials contained in GERANIOL COEUR™ synthetic which are of unknown constituency.

The GERANIOL COEUR™ synthetic and GERANIOL COEUR™ natural can also be tested in the olfactometer of FIGS. 3A, 3B and 3C using GERANIOL COEUR™ natural and/or GERANIOL COEUR™ synthetic absorbed on polyethylene pellets (for example, those manufactured by the Chromex Corporation of Brooklyn, N.Y.). Such polyethylene pellets are microporous polyethylene pellets which are called:

Innerflow/P75 Polyethylene Pellets

The following Examples set forth processes for preparing GERANIOL COEUR™ natural (Example I, infra) and GERANIOL COEUR™ synthetic (Example II, infra,). All parts are by weight unless otherwise specified.

EXAMPLE I

Preparation of GERANIOL COEUR™ Natural

Palmarosa oil is steam distilled from wild growing, fresh grass of the plant *Cymbopogon Martini*, varietas motia grown in Northeast Katmandu, Nepal. One part of Palmarosa oil is admixed with 4 parts of a 50:50 mixture of sodium hydroxide and methyl alcohol. The resulting mixture is heated at reflux for a period of one hour. 3.5 Parts of anhydrous methanol is then added to the resulting mixture. The resulting mixture is then steam distilled at 100 mm/Hg pressure. GERANIOL COEUR™ natural distills as the middle cut having a refractive index of 1.469–1.475 and a specific gravity at 20°/4° C. of 0.869–0.877. FIG. 4 is the GLC profile for the GERANIOL COEUR™ natural.

EXAMPLE II

Preparation of GERANIOL COEUR™ Synthetic

100 Grains of citronella oil (Java) is admixed with 50 ml of heptane. The resulting mixture is heated on a boiling water bath at 100° C. in a 1 liter flask for a period of one hour. At the end of the one hour period, 8 grams of sodium metal are slowly added to the resulting mixture. The addition of sodium metal takes place over a period of 0.5 hours. The resulting mixture is then filtered. Unreacted sodium is removed and the filtered complex-containing oil is maintained at a temperature of 5° C. for a period of 10 hours. The resulting crystalline product is then filtered and weighs 32 grams. The resulting product is then hydrodistilled in a 2 liter flask with 1.5 liters of water. The hydrodistillate fractions of 100 ml are collected. After separating the aqueous phase from the organic phase, the resulting fractions are analyzed via tin layer chromatography. The fractions are as follows:

| FRACTION NO. | WEIGHT (Grams) | REFRACTIVE INDEX | DENSITY |
|---|---|---|---|
| 1 | 4.5 | 1.456 | 0.8535 |
| 2 | 7.1 | 1.468 | 0.868 |
| 3 | 6.9 | 1.469 | 0.873 |
| 4 | 6.5 | 1.473 | 0.8755 |

Fractions 2, 3 and 4 are then combined to form GERANIOL COEUR™ synthetic. The GLC profile for the GERANIOL COEUR™ synthetic is set forth in FIG. 5.

What is claimed is:

1. A method for inhibiting from feeding the insect species *Blattella germanica* from a surface or volume inhabited by said *Blattella germanica* and containing an insect species feedant, consisting of the step of applying to the said surface or said volume a *Blattella germanica*-anti-feedant quantity and concentration of a geraniol-containing mixture comprising essentially of:

(i) nerol having the structure:

(ii) citronellol having the structure:

(iii) geraniol having the structure:

(iv) β-citronellol having the structure:

(v) 3,7-dimethyl octanol-1 having the structure:

OH ; and (vi) β-elemene having the structure:

defined according to the GLC profile of FIG. 4 and having a refractive index at a temperature of from 20° C. up to 25° C. in the range of from 1.469 up to 1.475 and a density at a temperature of from 20° C. up to 25° C. in the range of from 0.869 up to 0.877.

2. The method of claim 1 wherein the geraniol-containing composition is contained in a microporous polymer.

3. A method for inhibiting from feeding the insect species *Blattella germanica* from a surface or volume inhabited by said *Blattella germanica* and containing an insect species feedant, consisting of the step of applying to the said surface or said volume a *Blattella germanica*-anti-feedant quantity and concentration of a synthetic geraniol-containing mixture comprising essentially of:

(i) nerol having the structure:

(ii) citronellol having the structure:

(iii) geraniol having the structure:

OH ; and (iv) 3,7-dimethyl octanol-1 having the structure:

defined according to the GLC profile of FIG. 5 and having a refractive index at a temperature of from 20° C. up to 25° C. in the range of from 1.456 up to 1.473 and a density at a temperature of from 20° C. up to 25° C. in the range of from 0.8535 up to 0.8755.

4. The method of claim 3 wherein the geraniol-containing composition is contained in a microporous polymer.

* * * * *